United States Patent [19]

Lalauze et al.

[11] Patent Number: 4,485,667
[45] Date of Patent: Dec. 4, 1984

[54] METHOD, SENSOR AND DEVICE FOR DETECTING TRACE QUANTITIES OF GASES IN A GASEOUS MEDIUM

[75] Inventors: René Lalauze, Saint-Etienne; Christophe Pijolat, Vaulx-en-Velin; Jean-Paul Couput, Saint-Etienne, all of France

[73] Assignee: Association pour la Recherche et la Developpement des Methodes et Processus Industriels (Armines), France

[21] Appl. No.: 428,439

[22] Filed: Sep. 29, 1982

[30] Foreign Application Priority Data

Oct. 16, 1981 [FR] France ............................ 81 19536

[51] Int. Cl.³ .......................................... G01N 27/00
[52] U.S. Cl. ..................................... 73/23; 73/27 R; 422/98; 338/34
[58] Field of Search ................. 73/23, 27 R, 1 G; 338/34; 324/71.5; 340/634; 422/98

[56] References Cited

U.S. PATENT DOCUMENTS 3,999,947 12/1976 Mihara et al. ................... 73/23 X
4,169,369 10/1979 Chang ................................. 73/23
4,250,737 2/1981 Biglin .................................. 73/23

FOREIGN PATENT DOCUMENTS 2304080 10/1976 France .
1474080 5/1977 United Kingdom .
2002124 2/1979 United Kingdom .

Primary Examiner—Stephen A. Kreitman
Assistant Examiner—Vincent P. Kovalick
Attorney, Agent, or Firm—Gerald J. Ferguson, Jr.; Joseph J. Baker

[57] ABSTRACT

An enclosure (17) contains two ovens (18, 19) each containing a semiconductor metal oxide ($SnO_2$ or NiO) sensor (13) previously activated using $H_2S$ or $SO_2$. The sensors (13) are heated to different temperatures the lower of which corresponds to a peak on the sensor conductivity curve characteristic of the gas. The signals produced are applied to a comparator (30). For many toxic gases this peak occurs at concentrations below their toxicity threshold in air.

12 Claims, 6 Drawing Figures

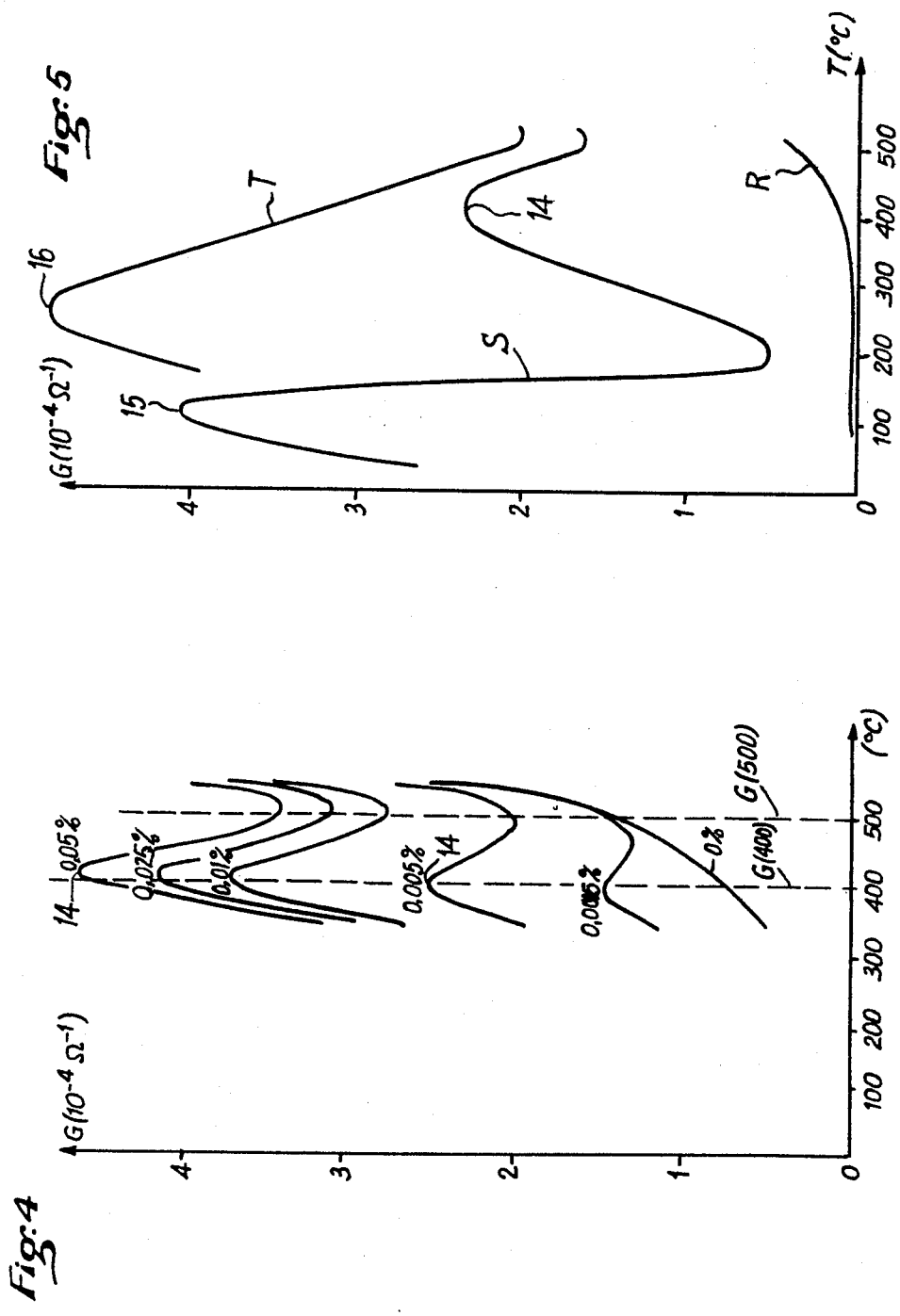

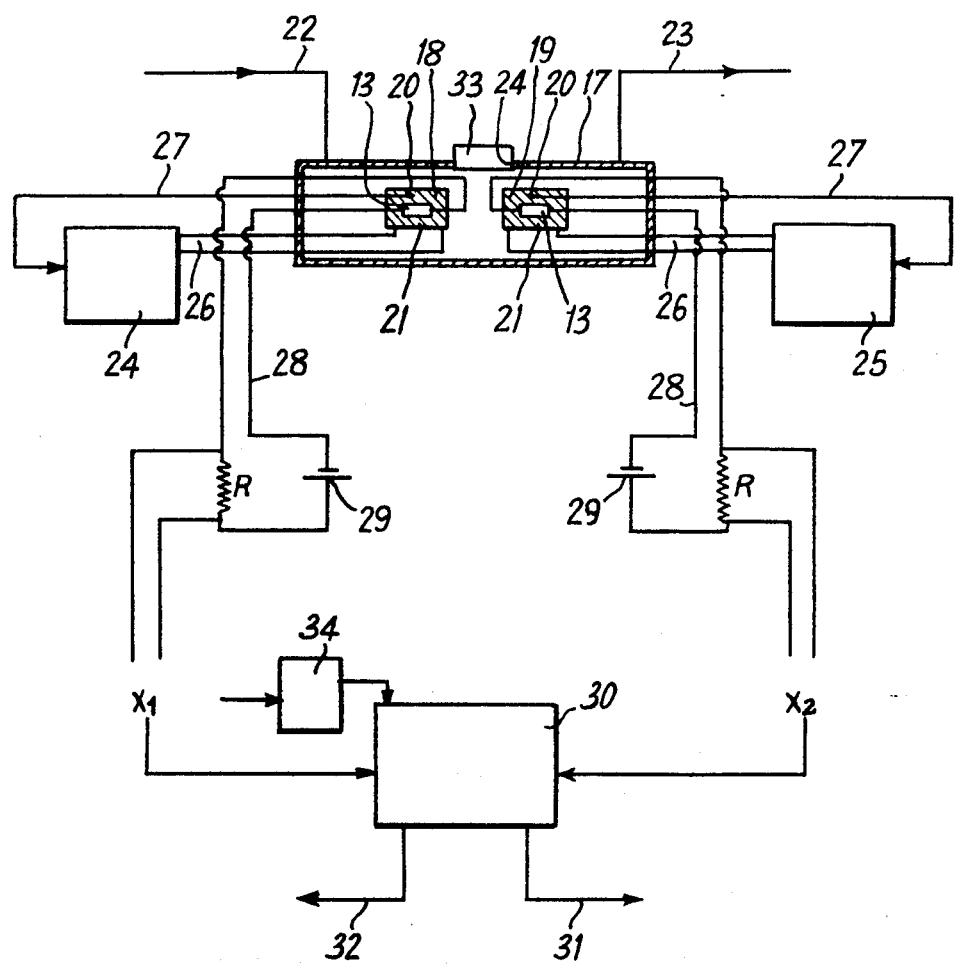

METHOD, SENSOR AND DEVICE FOR DETECTING TRACE QUANTITIES OF GASES IN A GASEOUS MEDIUM

BACKGROUND OF THE INVENTION

1. Field of the Invention

The invention concerns a method for detecting trace quantities of gases or gaseous impurities in a gaseous medium or in a monitored atmosphere by measuring the electrical conductivity of a sensor fabricated from a metal oxide selected from the group comprising $SnO_2$ and NiO, in which method said sensor is placed in a detector device in which it is heated and exposed to and/or supplied with the gaseous medium to be monitored. The invention also concerns a metal oxide sensor of this type and a device for implementing the method and comprising the sensor.

2. Description of the Prior Art

The semiconducting properties of certain metal oxides are well known. Their electrical conductivity varies as a function of temperature and in the presence of certain gases. These properties have been used for the detection of trace quantities of gases or gaseous impurities. The oxides used for this purpose are generally tin oxide $SnO_2$ and nickel oxide NiO. They are used in the crystalline state or in the form of a layer deposited on a ceramic support or in the form of pellets of sintered powder. Applications of this kind are described, inter alia, in U.S. Pat. Nos. 3,635,756, 3,900,815 and 4,039,941.

A great number of gases affect the conductivity of these oxides, however, as a result of which they are not very reliable when used as detector sensors, for want of a specific or selective action.

The invention, to be disclosed in detail later, is based on the discovery of a treatment which confers on the aforementioned semiconductor oxides electrical conductivity characteristics of an entirely novel kind permitting the selective detection of specific gases or groups of gases.

As a general rule, semiconductor oxides have an electrical conductivity $\sigma$ which varies with temperature and with the nature and pressure of the gases constituting its surrounding environment:

$\sigma$ increases exponentially with temperature, the sense in which $\sigma$ changes depends on the nature of the gas, the amplitude of the change depends on the partial pressure of the gases and the composition of the gaseous phase.

Chemisorption of a gas by a semiconductor oxide involves a transfer of electrons between the gas and the oxide. Depending on whether the gas g has a higher or lower affinity for electrons than the oxide s, there is a transfer of electrons from the solid to the gas ($s^+-g^-$) or from the gas to the solid ($s^--g^+$), respectively. This transfer contributes to an increase or decrease in the number of free majority carriers in the solid. The sense of the variation is defined by the type of bond ($g^+-s^-$ or $g^--s^+$) and by the nature of the majority carriers, that is to say electrons in the case of n type semiconductors and holes in the case of p type semiconductors.

It is known that the electrical conductance G of a semiconductor is substantially proportional to the number of majority carriers. Consequently, the presence of a gas varies the conductance of the semiconductor according to whether the gas adsorbed takes up electrons from or donates electrons to the semiconductor.

It is then said to be either an electron acceptor or donor, respectively.

If the gas is an acceptor and if the semiconductor metal oxide is of type n, the gas takes an electron from the solid, the conductance of which diminishes. If the gas is an acceptor and the semiconductor metal oxide is of type p, the gas takes an electron from the solid, the conductance of which increases.

If the gas is a donor, the senses of the electrical variations observed will be the inverse of those just defined. In other words, for a specific gas there is always observed a variation in conductivity according to the concentration of the gas. It is therefore only necessary to measure such variation in order to detect the presence of this gas. The sensors currently used and based on this principle are relatively sensitive in practice, but they have the major disadvantage of offering an electrical response which does not provide for selective or specific detection of a given gas in a mixture.

The objective of the invention is to propose a new method, sensor and device for selective detection of gases with a very high degree of sensitivity.

SUMMARY OF THE INVENTION

The invention consists in a method for detecting trace quantities of gases or gaseous impurities in an atmosphere by measuring the electrical conductivity of a sensor fabricated from a metal oxide selected from the group comprising $SnO_2$ and NiO at a maximum temperature of approximately 500° C. and processed, prior to utilization, by exposure to a flow of gas containing an activating gas selected from the group comprising $SO_2$ and $H_2S$ at substantially the same temperature, with a maximum of approximately 550° C., in which method said sensor is placed in a detector device in which it is heated and exposed to an atmosphere to be monitored.

While working on the development of a sensor specific to benzene, the inventors noticed that certain sensors showed a peak at around 400° C. on the curve G=f(T) (G=conductance, T=temperature) in a benzene atmosphere, for concentrations of 0.001% or less, significantly below the toxicity threshold, which is 0.0035%. Some of these sensors were sintered from oxide powder, while others were fabricated by depositing oxide powder on a ceramic support. Following a critical examination of the results obtained and systematic tests, the inventors were able to establish that:

1. The peak moves in the direction of increasing temperature and reduces the intensity to the point of disappearing completely if the sensor is raised to too high a temperature, of the order of 550° C.
2. The peak occurs only if the sensor has previously been exposed to $SO_2$ or $H_2S$. This treatment is irreversible unless the sensor is treated by saturating it for several hours, for example.

These two observations are embodied in the essential feature of the invention.

Mention should also be made of the effect of water absorbed by the sensor, producing an abnormal peak at 250° C. when the temperature is raised in moist air, and a plateau at the level of the peak around 400° C. when the temperature is reducing. Such humidity conditions rarely occur under normal operating conditions, however.

In a preferred embodiment, the sensor is fabricated from the metal oxide using the sintering process which is known per se. This fabrication process is preferred as it facilitates good contact with the power supply and measuring electrodes and because it facilitates machining of the sensor.

In accordance with the invention, the flow of gas is a flow of air or a neutral gas containing approximately 0.1% of the activating gas. The sensor is exposed to the flow of gas containing the activating gas for between 30 seconds and 5 minutes.

Detection of the characteristic peak is facilitated by raising the sensor to two different temperatures, the lower of which corresponds to that of the peak for the gas to be detected, while it is being exposed to the atmosphere being monitored. The sense of the change and/or difference between the respective conductivity values at each of said temperatures is measured as representative of the presence and/or concentration of a gaseous impurity.

In one embodiment, the sensor is raised to said temperatures successively, but in a preferred embodiment two identical sensors are used simultaneously, and each is raised to one of said temperatures.

In either case, the two temperatures differ by approximately 100° C. and the lower temperature is approximately 100° C. for $H_2S$, 200° C. for $SO_2$, 400° C. for benzene, 250° to 275° C. for carbon tetrachloride, diethyl ether, butyl acetate, butanol and acetaledehyde, 300° to 325° C. for toluene and chloroform, 325° to 350° C. for hexane, 375° C. for cyclohexane.

These characteristics of the invention are based on the observation of conductivity peaks specific to the designated gas or gases at the lower of the two temperatures.

These characteristics show that it is possible to detect selectively $H_2S$, $SO_2$, a hydrocarbon or a toxic derivative of the group designated. Assuming that the gas analyzed is one of the designated gases and when using two temperatures as explained hereinabove, the sensor operating at the lower temperature, that is to say in the vicinity of the peak previously referred to, produces an electrical signal higher than that produced by the sensor operating at the higher temperature, whereas in the absence of this gas the electrical signal varies with temperature.

The invention further consists in a sensor for detecting trace quantities of gases or gaseous impurities in an atmosphere by measuring its electrical conductivity, fabricated from a metal oxide selected from the group comprising $SnO_2$ and NiO at a maximum temperature of 550° C. and activated by exposure to a flow of gas containing a gas selected from the group comprising $SO_2$ and $H_2S$.

In its practical embodiment, the invention consists in a device comprising an oven, means for adjusting the temperature of said oven, a sensor in said oven fabricated from a metal oxide selected from the group comprising $SnO_2$ and NiO and activated by means of a flow of gas containing a gas selected from the group comprising $SO_2$ and $H_2S$, electrical power supply means for said sensor, means for detecting a signal produced by said sensor in response to variation in one of its electrical parameters, means for introducing part of the monitored atmosphere into said oven and removing same therefrom, means for setting the oven temperature to two consecutive values, means for storing said electrical signal from said sensor at one of said temperatures and means for comparing said stored signal with the signal produced by said sensor at the other temperature.

The invention further consists in an alternative embodiment in which the aforementioned device comprises a second oven and a second sensor, means for setting the temperatures of said ovens to different values and means for comparing said signals produced by said sensors.

Other objects and advantages will appear from the following description of an example of the invention, when considered in connection with the accompanying drawings, and the novel features will be particularly pointed out in the appended claims.

BRIEF DESCRIPTION OF THE DRAWINGS

FIG. 4 is a graph showing the variation in the conductance of a sensor in accordance with the invention as a function of temperature for various concentrations of benzene in air.

FIG. 5 is graph showing the variation in the conductance of a sensor in accordance with the invention as a function of temperature in pure air and in air containing detectable impurities.

FIG. 6 is a schematic showing a detector device in accordance with the invention.

DESCRIPTION OF THE PREFERRED EMBODIMENTS

Figure 1:
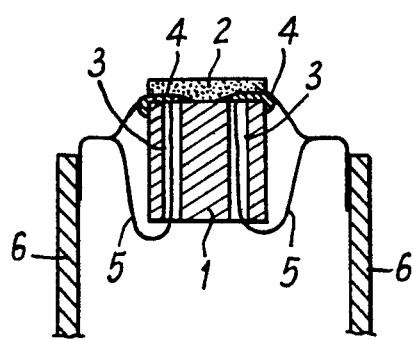
FIG. 1 is a schematic cross-section through a sensor in accordance with the invention, considerably enlarged.
Figure 2:
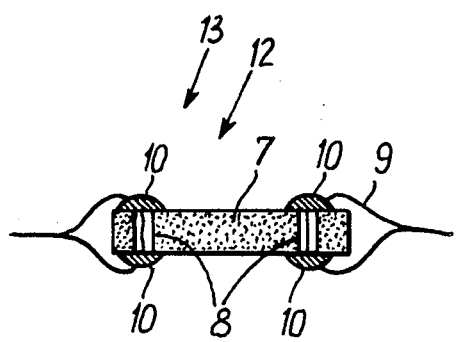
FIG. 2 is a view analogous to FIG. 1 of an alternative form of sensor.

FIGS. 1 and 2 show two sensors in accordance with the invention, much enlarged.

Referring to FIG. 1, an alumina support 1 is covered with a layer 2 approximately 1 mm thick of powdered $SnO_2$ or NiO deposited from a suspension in ethanol. The alumina support is formed with two holes 3 which open under layer 2. Two contact seals 4 in gold paste provide electrical contact with respective platinum contact wires 5 disposed in the form of loops and each connected to an electrode 6. Prior to utilization, the sensor is exposed to a flow of air containing 0.1% of $SO_2$ or $H_2S$ at a temperature of 550° C. for between 30 seconds and 5 minutes, and preferably for 3 minutes.

FIG. 2 shows a sensor fabricated using the preferred sintering process. Starting with powdered $SnO_2$ or NiO with a particle size of 50 to 100 μm, a pellet is formed at a pressure of 2 t applied for one minute at ambient temperature. The resulting pellet is then held at 500° C. for 10 minutes and then exposed, also at 500° C., to a flow of air containing 0.1% of $SO_2$ or $H_2S$, for between 30 seconds and 5 minutes and preferably for 3 minutes. The result is a sintered activated pellet 7 formed with two holes 8 each accommodating a contact wire 9 disposed in a loop and sealed at each side of hole 8 by a dab of gold paste 10.

Either process produces a sensor 11 or 12 which, in the remainder of this description, will be referred to as "sensor 13" with no other distinction. There is no functional difference between the two, which are distinguished by their resistance to wear, which is better in the case of the sintered sensor 12.

Figure 3:
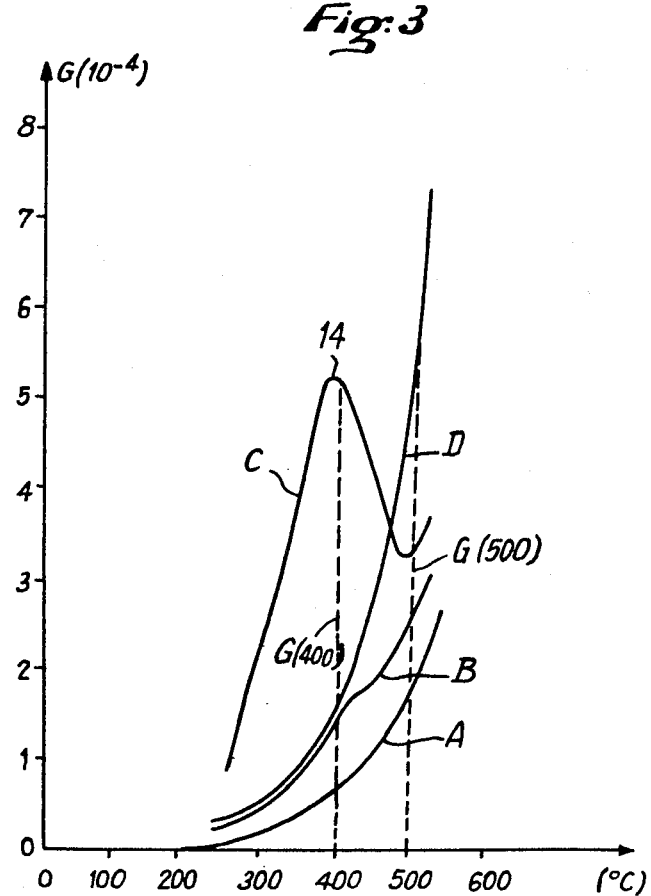
FIG. 3 is graph showing the variation in the conductance of a sensor in accordance with the invention as a function of temperature for certain gaseous compounds.

How the sensor in accordance with the invention behaves in the presence of benzene or other gases will now be described with reference to FIG. 3, along the abscissae of which is plotted the temperature in °C. to which the sensor is raised and along the ordinates of which is plotted its conductance G expressed in $10^{-4}\Omega^{-1}$. Curve A shows the relationship between conductance and temperature for an activated sensor exposed to pure air. Curve B shows the same relationship for a non-activated sensor (not part of the invention) exposed to air containing 0.1% benzene. Curve C relates to an activated sensor in accordance with the invention exposed to air containing 0.012% benzene. Curve D relates to a sensor in accordance with the invention exposed to air containing 0.04% $CH_4$. The presence of benzene produces a characteristic peak 14 at approximately 400° C. in the curve for the sensor in accordance with the invention. The method in accordance with the invention is based on the use of this property and measurement of G(500)−G(400), which has a positive value in the absence of benzene and a negative value in the presence of benzene. Referring to FIG. 4, it will be seen that the difference G(500)−G(400) varies significantly as a function of the percentage of benzene in the range shown (0% to 0.05% concentration). There is a peak 14 in the value of G increasing with benzene concentration, and a negative difference increasing in absolute value between G(500) and G(400).

FIG. 5 shows, using the same co-ordinates as FIG. 4 and for a sensor in accordance with the invention activated using $SO_2$, the curve R obtained in pure air and the curve S obtained with air containing 0.004% $H_2S$ and 0.1% benzene. It includes the peak 14 at approximately 400° C. (characteristic of benzene) and a peak 15 at approximately 100° C. (characteristic of $H_2S$). The curve T shows a peak 16 which corresponds to air containing 0.1% $SO_2$.

Other tests have been carried out to draw up a list of the peaks characterizing most of the usually recognized toxic gases and vapors, indicated below with their toxicity threshold expressed as a percentage:

Carbon tetrachloride (0.005): 250° to 275° C. approx,
Toluene (0.02): 300° to 325° C. approx,
Chloroform (0.01): 300° to 325° C. approx,
Butyl acetate (0.02): 250° C. approx,
Diethylether (0.04): 250° to 275° C. approx,
Methylethylcetone: 250° to 275° C. approx,
Hexane (0.05): 325° to 350° C. approx,
Butanol (0.005): 250° to 275° C. appox,
Acetaldehyde (0.02): 275° C. approx,
Cyclohexane (0.04): 375° C. approx.

For all these products, the peak appears below the toxicity threshold.

A peak is also observed for the following hydrocarbons:

Pentane: 400° C. approx,
Butane: 425° C. approx,
Ethylene: 425° C. approx.

This shows that it is possible to detect in a selective manner either benzene alone or selected groups of toxic products by measuring the conductance of a sensor at the temperature of the peak and that of another sensor at a significantly (approximately 100° C.) higher temperature and comparing the two.

The device in accordance with the invention and its operation and use will now be described with reference to FIG. 6.

A device in accordance with the invention comprises an enclosure 17 in which are disposed two ovens 18 and 19 each containing a sensor 13 in accordance with the invention. Sensors 13, if of the sintered type are ground down to a size of approximately 2×5 mm. Ovens 18 and 19 are cylindrical, with a length of 20 mm and a diameter of 8 mm. They are formed by winding a 0.1 mm diameter Kanthal wire onto a quartz tube. An asbestos braid separates the turns. The complete assembly is encapsulated in refractory cement. A thermocouple 20 is embedded in the cement for monitoring the temperature of oven 18 or 19. The resulting measuring heads 21 are of compact dimensions. The two heads 21 are mounted in enclosure 17, which comprises a gas inlet 22 and a gas outlet 23. A window 24 permits the mounting of a sintered metal plug 33 for direct monitoring of the ambient atmosphere by diffusion. The ovens are connected to variable transformers connected to a 220 V AC supply. With approximately 10 turns, the two temperatures (400° C. and 500° C., for example) are easily obtained at approximately 30 V and 0.4 A. Ovens 18 and 19 are heated by respective electrical power supplies 24 and 25 and connecting lines 26, each electrical power supply being controlled by a connecting line 27 from the corresponding thermocouple 20.

The sensor terminals 6 and 9 are connected by circuits 28 to a measuring circuit connected to a supply 29 and comprising a resistor R across which appears signal $X_1$ in the case of oven 18 and $X_2$ in the case of oven 19. Each signal is proportional to the conductance G of the associated sensor. Signals $X_1$ and $X_2$ are applied to a sense discriminating comparator 30. Comparator 30 is connected to an alarm circuit (not shown) via line 31 and to an $X_1-X_2$ measuring circuit (not shown) via line 32.

OPERATION

The apparatus is easy to use.

The temperature of one oven (18, for example) is adjusted to a value in the vicinity of the temperature at which the peak characteristic of the gas or family of gases to be selectively detected is known to occur. The temperature of the other oven 19 is set approximately 100° C. higher than that of the first oven 18. Part of the atmosphere to be monitored is passed in pulsed manner continuously into the enclosure, or enclosure 17 is placed in the atmosphere so that diffusion can occur through window 24. If the gas to be detected is present in a concentration exceeding its detection threshold, which is very low (0.015% for benzene, the toxicity threshold of which is 0.035%), signal $X_1-X_2$, previously negative (see FIG. 4), becomes positive, causing a reaction from comparator 30. As required by the user, the comparator can trip an alarm from a determined threshold and/or record and/or display the value of the difference $X_1-X_2$.

It will be appreciated that it is also possible, where the toxic concentration varies slowly, to use a single sensor raised successively to the temperature of the peak and to a temperature 100° C. higher, on condition that a device 34 for storing the value $X_1$ is provided and this value is sent to comparator 30 only when value $X_2$ has been measured.

It will be understood that various changes in the details, materials and arrangements of parts, which have been herein described and illustrated in order to explain the nature of the invention, may be made by those skilled in the art within the principle and scope of the invention as expressed in the appended claims.

For example, more than two sensors may be used for selective detection of two gases or family of gases with characteristic peaks at different temperatures.

About the layer deposited on a ceramic support it will be understood that one may use a thin layer of several tenths or hundreds Å or a thicker layer with the same result.

What we claim is:

1. A method for detecting trace quantities of gases or gaseous impurities in an atmosphere by measuring the electrical conductivity of a sensor fabricated from a metal oxide selected from the group comprising $SnO_2$ and NiO at a maximum temperature of approximately 500° C. and processed, prior to utilization, by exposure to a flow of gas containing an activating gas selected from the group comprising $SO_2$ and $H_2S$ at substantially the same temperature, with a maximum of approximately 550° C., in which method said sensor is placed in a detector device in which it is heated and exposed to an atmosphere to be monitored.

2. A method according to claim 1, wherein said sensor is fabricated using the sintering process for depositing a layer on a ceramic support.

3. A method according to claim 1, wherein said flow of gas is a flow of air or a neutral gas containing approximately 0.1% of said activating gas.

4. A method according to claim 1, wherein said sensor is exposed to said flow of gas containing said activating gas for between thirty seconds and five minutes, and preferably for three minutes.

5. A method according to claim 1, wherein said sensor is raised to two different temperatures while it is being exposed to and/or supplied with the atmosphere being monitored and the sense of the change and/or difference between the respective conductivity values as each of said temperatures is measured as representative of the presence and/or concentration of the gaseous impurity.

6. A method according to claim 5, wherein said sensor is raised to said temperatures successively.

7. A method according to claim 5, wherein two identical sensors are used simultaneously, and each is raised to one of said temperatures while it is being exposed to and/or supplied with the atmosphere being monitored and the sense of the change and/or difference between the respective conductivity values at each of said temperatures is measured as representative of the presence and/or concentration of the gaseous impurity.

8. A method according to claim 5, wherein said trace quantities are selected from the group consisting of $H_2S$, $SO_2$, benzene, pentane, carbon tetrachloride, diethylether, butyl acetate, butanol, acetaldehyde, toluene, chloroform, hexane, cyclohexane, butane and ethylene, and wherein said temperatures differ by approximately 100° C. and the lower temperature is approximately 100° C. for $H_2S$, 200° C. for $SO_2$, 400° C. for benzene and pentane, 250° to 275° C. for carbon tetrachloride, diethylether, butyl acetetate, butanol and acetaldehyde, 300° to 325° C. for toluene and chloroform, 325° to 350° C. for hexane, 375° C. for cyclohexane, 425° C. for butane and ethylene.

9. An activated sensor for detecting trace quantities of gases or gaseous impurities in an atmosphere by measuring its electrical conductivity, said sensor comprising a metal oxide selected from the group comprising $SnO_2$ and NiO activated by a gas selected from the group comprising $SO_2$ and $H_2S$.

10. A device for implementing a method for detecting trace quantities of gases or gaseous impurities in an atmosphere by measuring the electrical conductivity of a sensor fabricated from a metal oxide selected from the group comprising $SnO_2$ and NiO at a maximum temperature of approximately 500° C. and processed, prior to utilization, by exposure to a flow of gas containing an activating gas selected from the group comprising $SO_2$ and $H_2S$ at substantially the same temperature, with a maximum of approximately 550° C., in which method said sensor is placed in a detector device in which it is heated and exposed to an atmosphere to be monitored, in which device said sensor is raised to two different temperatures while it is being exposed to and/or supplied with the atmosphere being monitored and the sense of the change and/or difference between the respective conductivity values at each of said temperatures is measured as representative of the presence and/or concentration of the gaseous impurity, said device comprising an oven, means for adjusting the temperature of said oven, a sensor in said oven fabricated from a metal oxide selected from the group comprising $SnO_2$ and NiO and activated by means of a flow of gas containing a gas selected from the group comprising $SO_2$ and $H_2S$, electrical power supply means for said sensor, means for detecting a signal produced by said sensor in response to variation in one of its electrical parameters, means for introducing part of the monitored atmosphere into said oven and removing same therefrom, means for setting the oven temperature to two consecutive values, means for storing said electrical signal from said sensor at one of said temperatures and means for comparing said stored signal with the signal produced by said sensor at the other temperature.

11. A device for implementing a method for detecting trace quantities of gases or gaseous impurities in an atmosphere by measuring the electrical conductivity of a sensor fabricated from a metal oxide selected from the group comprising $SnO_2$ and NiO at a maximum temperature of approximately 500° C. and processed, prior to utilization, by exposure to a flow of gas containing an activating gas selected from the group comprising $SO_2$ and $H_2S$ at substantially the same temperature, with a maximum of approximately 550° C., in which method said sensor is placed in a detector device in which it is heated and exposed to an atmosphere to be monitored, and in which device two identical sensors are used simultaneously, and each is raised to one of said temperatures while it is being exposed to and/or supplied with the atmosphere being monitored and the sense of the change and/or difference between the respective conductivity values at each of said temperatures is measured as representative of the presence and/or concentration of the gaseous impurity, said device comprising two subsystems each of which comprises an oven, means for adjusting the temperature of said oven, a sensor in said oven fabricated from a metal oxide selected from the group comprising $SnO_2$ and NiO and activated by means of a flow of gas containing a gas selected from the group comprising $SO_2$ and $H_2S$, electrical power supply means for said sensor, means for detecting a signal produced by said sensor in response to variation in one of its electrical parameters, means for introducing part of the monitored atmosphere into said oven and removing same therefrom, means for setting the temperatures of said ovens to different values and means for comparing said signals produced by said sensors.

12. A device according to claim 11, wherein said two ovens are disposed in a common enclosure comprising said means for introducing part of the monitored atmosphere into said oven and removing same therefrom.

* * * * *